United States Patent [19]

Kawazoe et al.

[11] Patent Number: 4,576,146

[45] Date of Patent: Mar. 18, 1986

[54] FIBERSCOPE

[75] Inventors: Chisato Kawazoe; Kenichi Yoshida; Koichi Tsuno, all of Osaka, Japan

[73] Assignee: Sumitomo Electric Industries, Ltd., Osaka, Japan

[21] Appl. No.: 592,210

[22] Filed: Mar. 22, 1984

[30] Foreign Application Priority Data

Mar. 22, 1983 [JP] Japan ................... 58-48205

[51] Int. Cl.⁴ .................................. A61B 1/06
[52] U.S. Cl. ........................ 128/6; 350/96.26
[58] Field of Search ............ 128/3, 4, 5, 6, 7, 8, 128/9, 10, 11; 350/96.26

[56] References Cited

U.S. PATENT DOCUMENTS 2,691,370  10/1954  Wallace .......................... 128/6
3,349,762  10/1967  Kapany .......................... 128/6 X
3,866,599   2/1975  Johnson ......................... 128/6 X Primary Examiner—William H. Grieb
Attorney, Agent, or Firm—Sughrue, Mion, Zinn, Macpeak, and Seas

[57] ABSTRACT

A fiberscope for conducting observations in a region ordinarily filled with an opaque liquid, particularly, inside blood vessels or the heart. A recess is provided at a front end of a cover tube for accommodating a front end portion of an image fiber and a bundle of illuminating light transmitting optical fibers which are bonded to a light guide front end part molded to conform to a part of the inner wall of a cover tube, and an optical fiber bundle provided by bonding front end portions of the image fiber and the light guide is fixedly bonded to the inner wall of the cover tube. A transparent liquid, physiological saline in preferred embodiments, is injected from a hole near the end of the fiberscope at a flow rate determined in accordance with the flow rate of the opaque liquid to temporarily displace some of the opaque liquid to permit observation. Further, the injection of the transparent liquid may be done in synchronization with variations of the pressure and/or flow velocity of the opaque liquid.

8 Claims, 30 Drawing Figures

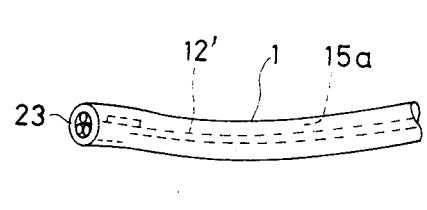
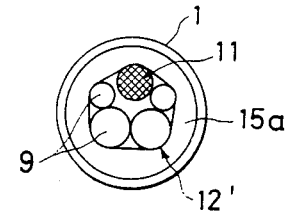
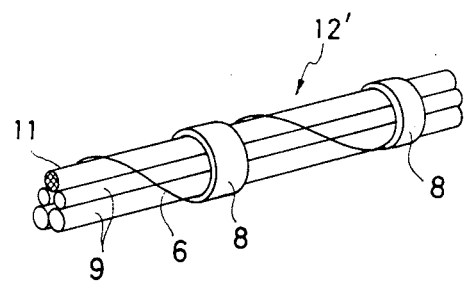
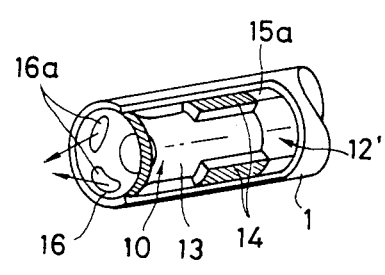
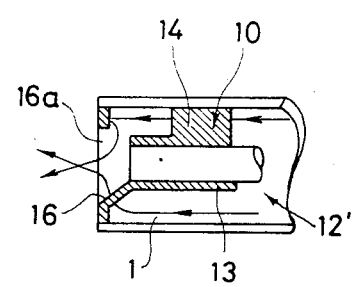

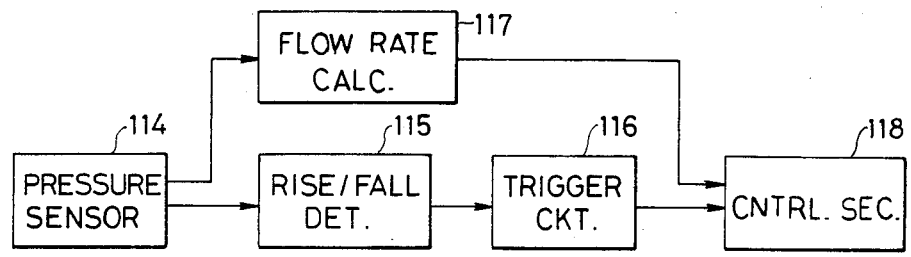
FIG. 14
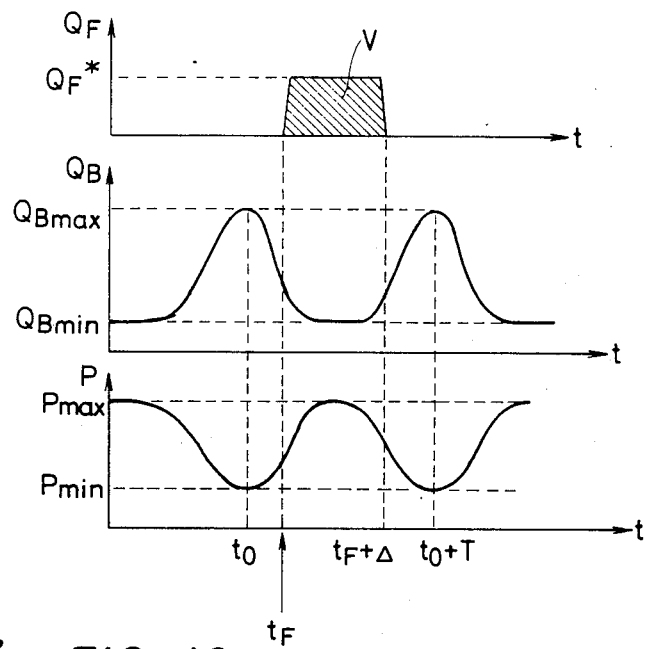
FIG. 15
FIG. 17   FIG. 16
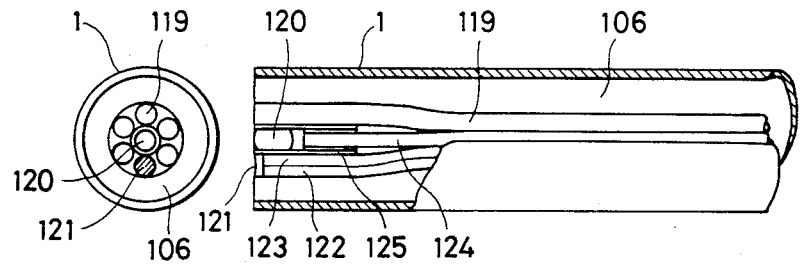

FIBERSCOPE

BACKGROUND OF THE INVENTION

The present invention relates to fiberscopes. More particularly, the invention relates to a fiberscope for optically observing a region filled with opaque liquid such as the inside of a blood vessel or the heart.

FIGS. 1 and 2 are explanatory diagrams showing a conventional fiberscope. A flexible tube 1 includes illuminating light transmitting light guides and an image fiber for directly transmitting an image. The former is coupled to an illuminating light source 3, and the latter is coupled through an image receiving adapter 2 to a light-receiving unit such as a 16-mm movie camera or a television camera.

More specifically, the flexible tube 1 encases light guides 9 for transmitting illuminating light from a light source 3 to a region 5 to be observed (the inside of a blood vessel 7 as shown in FIG. 2), an image transmitting image fiber 11 having at the forward end thereof a lens for forming the image of an object, and a liquid guide passage for introducing a physiological saline solution from a syringe 13 to the observation region 5 in front of the light guides 9 and the image forming lens of the image fiber 11 to form a transparent region. In order to provide the transparent physiological saline region in the flow of blood as described above, it is necessary to eject the saline solution from the end of the fiberscope at a flow rate at least substantially equal to that of the blood at that point, typically, about 50 cm³/sec.

FIG. 3 shows a cross-sectional view of the flexible tube in a conventional fiberscope. A liquid guide passageway 15 having a circular cross section is disposed between a tube 1 and light guides 9, which also have circular cross sections. In this case, the outside diameter of the tube 1 is necessarily limited (4 mm for instance), and accordingly it is impossible to increase the effective cross-sectional area of the liquid guide passage 15 through which the saline solution passes, and hence it is also impossible in many instances to inject the saline solution at a sufficiently high flow rate.

A transparent region may be formed at the front end of the fiberscope by employing, instead of a flush of physiological saline, a transparent balloon attached to the front end of the fiberscope which is inflated for observation. However, this technique suffers from the drawback that the flow of blood is stopped in a small diameter blood vessel.

FIG. 4 shows a cross-sectional view of another example of a conventional fiberscope. In this conventional fiberscope, a fiber bundle 12 includes light guides 9 and an image fiber 11, and the liquid guide passage 15 is provided between the tube 1 and an outer peripheral surface of the fiber bundle 12. With this structure, the cross-sectional area of the liquid guide passage 15 is larger than that of the first conventional example shown in FIG. 3. However, the effective cross-sectional area is still limited due to the limitation of the outer diameter of the tube 1. Therefore, a sufficient flush may not be obtainable as in the first conventional example.

Further, in the fiberscope, in order to separate the liquid guide passageway 15, which communicates with the syringe 13, from the fiber bundle 12, including the light guides 9 coupled to an image pickup unit 4 and the image fiber 11, a branching section 19 is provided at the rear end of the tube. The structure of the conventional branching section is as shown in FIG. 5. A small hole 21 is formed in the wall of the flexible tube 1, and the fiber bundle 12, including the light guides 9 and the image fiber 11, extends through the small hole 21. The small hole is covered with a silicon resin layer 23 formed by coating, and an epoxy resin layer 25 is molded over the silicon resin layer. Then, the tube 1, the silicon resin layer, and the epoxy resin layer are wrapped with a tape 27.

This structure of the conventional branching section is disadvantageous in the following points:

(1) Since the flexible tube 1 in which is formed the small hole 21 is soft, the position of the small hole is unstable during the resin coating and molding process and in wrapping the tube with tape, as a result of which the sealing effect is liable to be unsatisfactory.

(2) Since the resin molding proccess, or the tape wrapping operation, takes a relatively long time, the manufacturing cost is high.

(3) At the branching section, the fiber bundle 12 is supported by the soft flexible tube 1, and hence it is not sufficiently stiff.

(4) The outermost layer of the branching section is formed by manually wrapping the tube, the silicon resin layer and the epoxy resin layer with tape. Therefore, the external appearance of the branching section is poor.

An improvement to obtain a sufficient amount of flushing solution is disclosed in commonly assigned copending U.S. application Ser. No. 561,705, filed Dec. 15, 1983.

FIGS. 6–10 shows the fiberscope described in the copending application. The blood vessel insertion section of the fiberscope includes a flexible tube 1 housing a fiber bundle 12' composed of an image fiber 11, having a lens for forming the image of the object under observation at its front end, and light guides 9. A liquid guide passageway 15a for introducing physiological saline solution is formed between the inner wall of the cover tube 1 and the outer wall of the fiber bundle 12'. The fiber bundle 12' is formed by bundling the image fiber 11 and the light guides 9 with a thin binding thread or tape 6 and then wrapping them with small bands 8 made of a heat-shrinkable material. The fiber bundle 12' thus formed is loosely inserted into the cover tube 1, except for an area near its front end portion. A cap 10 is provided at the end of the fiberscope to hold the fiber bundle 12' in the cover tube 1 in such a manner that the fiber bundle is held coaxial with the cover tube. The cap 10, as shown in FIGS. 9 and 10, is composed of a sleeve 13 for holding the front end portion of the fiber bundle 12', spacers 14 provided at equal intervals around the sleeve and bonded to the inner wall of the cover tube so that the sleeve is held coaxial with the cover tube, a concave front wall 16 extending inwardly from the front end of the sleeve 13 and bonded at its periphery to the inner wall of the cover tube 1, and outlets 16a formed in the front wall 16 to communicate with the liquid guide passage 15a. The inner surface of the front wall 16, as shown in FIG. 10, is formed as a guide wall for directing (as indicated by an arrow), on the upstream side of the outlets 16a, the flow of saline from the liquid guide passage 15a towards the front end face of the fiber bundle 12', that is, towards the lens at the front end of the image fiber 11 and the front end faces of the light guides 9.

With this structure, a large cross-sectional area of the liquid guide passage can be obtained within a limited space. However, the fiberscope thus constructed is still disadvantageous in the following points:

(1) In order to increase the flow rate of physiological saline solution, the pressure used for injecting the solution is necessarily high.

(2) For the same purpose, the outside diameter of the flexible cable is large, and accordingly the applications where the fiberscope can be employed are limited.

(3) Because of the large flow rate and large volume of flow of the physiological saline solution, adjacent tissues may be damaged.

(4) The cap 10 used for positioning the fiber bundle 12′ in the cover tube 1 in such a manner that the fiber bundle is held coaxial with the cover tube 1 has a considerably intricate structure to prevent as much as possible obstruction of the flow of saline solution. Therefore, the manufacturing cost of the cap 10 is necessarily high. Specifically, since the cap 10 is of a small size and must be produced by machining and molding, the production cost of the cap is high, thus making the manufacturing cost of the resultant fiberscope high.

(5) The contact area of the cap 10 and the cover tube 1 cannot be made as large as is desirable because of the cap structure. Therefore, the cap is not sufficiently bonded to the cover tube, and it may be dislodged from the tube by shocks which occur during flushes of physiological saline.

(6) Since the structure of the cap 10 is intricate as described above, it is difficult to provide a cap of small size. Accordingly, the outside diameter of the cover tube 1 is large, and therefore it is difficult to insert it into a blood vessel.

SUMMARY OF THE INVENTION

It is therefore an object of the present invention to overcome the above-mentioned drawbacks and to provide an improved optical fiberscope.

Another object of the invention is to provide a fiberscope capable of discharging an optimum amount of flushing liquid to provide a clear observation region, whereby the timing of the injection of the physiological saline solution and the flow rate thereof are determined according to the flow rate of the opaque liquid.

Still another object of the invention is to provide a fiberscope capable of being produced at low cost.

Yet another object of the invention is to provide a fiberscope wherein the strength of the seal at its branch portion is enhanced and the outer appearance is excellent.

According to the present invention, a fiberscope for conducting observations in a region ordinarily filled with an opaque fluid includes a fiber bundle including an image transmitting image fiber and associated optical system lens for forming and transmitting the image of an object under observation and illuminating light transmitting light guides arranged parallel to the image fiber, a cover tube covering the fiber bundle, and a liquid passageway for introducing transparent liquid. The liquid passageway, which is formed between the inner wall of the cover tube and the other surfaces of the fiber bundle, passes a transparent liquid to be injected in front of the optical system and light guides.

The fiberscope of the invention is particularly characterized in that transparent liquid is injected from a hole near the end of the fiberscope in an amount and at a flow rate determined in accordance with the flow rate and/or flow velocity of the opaque liquid. To this effect, the inventive fiberscope is provided with means for measuring a pressure and/or flow velocity of the opaque liquid near the end of the fiberscope. The timing of injection of the transparent liquid is determined by detecting variations of the pressure and/or flow velocity.

Further, according to the invention, a recess for accommodating the front end portion of the image fiber is provided, the front end portions of illuminating light transmitting optical fibers in a bundle are bonded together and are then bonded to a front end part of a light guide which is molded to conform in shape to a part of the inner wall of the cover tube, and an optical fiber bundle formed by bonding the front end portions of the image fiber and light guides to the aforementioned part of the inner wall of the cover tube.

Moreover, according to one embodiment of the invention, in place of the cap used in the conventional fiberscope, a spiral spacer, extending in the axial direction of the fiber bundle in the liquid passageway, is secured to the front end portion of the fiber bundle in such a manner that it maintain the fiber bundle in position along the axis of the cover tube and forms a liquid outlet.

Furthermore, at a branch portion of the fiberscope according to the present invention, the branching section of the fiber body and cover tube is covered and sealed by a rigid branching mount which is composed of upper and lower halves and has a tube guide passageway and a fiber guide passageway branched from the tube guide passageway. The branching section has a rigid structure, provides a satisfactory sealing function, and can be readily formed at low cost.

BRIEF DESCRIPTION OF THE DRAWINGS

In the drawings,

FIG. 6 is a perspective view showing a part of a fiberscope, disclosed in a copending application, which part is adapted to be inserted into a blood vessel;

FIG. 7 is a cross-sectional view of the fiberscope of FIG. 6;

FIG. 8 is a perspective view showing a part of a fiber bundle inserted into the fiberscope of FIG. 6;

FIG. 9 is a perspective view, with parts cut away, showing the front end portion of the fiberscope of FIG. 6;

FIG. 10 is a longitudinal sectional view of the front end portion of the fiberscope of FIG. 6;

FIG. 14 is a block diagram of a flush control circuit;

FIG. 15 is a diagram showing variations of blood pressure with time ad the flushing method employed;

FIGS. 16 and 17 are diagrams showing the end portion of a fiberscope with a blood pressure sensor;

DESCRIPTION OF THE PREFERRED EMBODIMENTS

Figure 1:
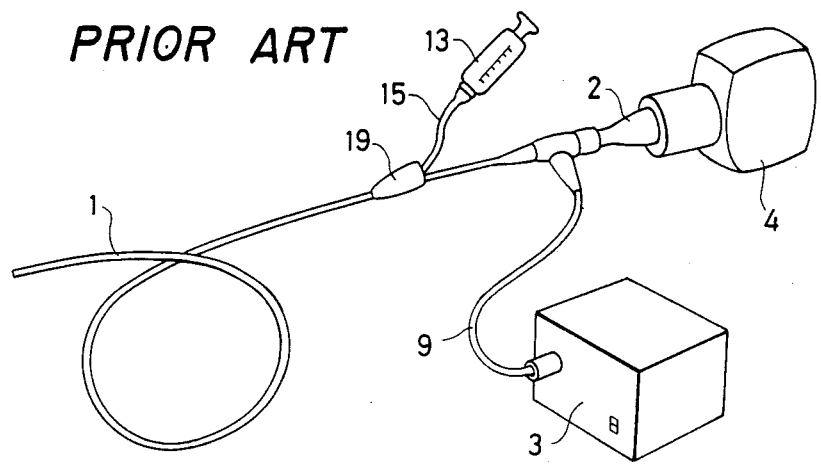
FIG. 1 is an external view of a conventional fiberscope.
Figure 2:
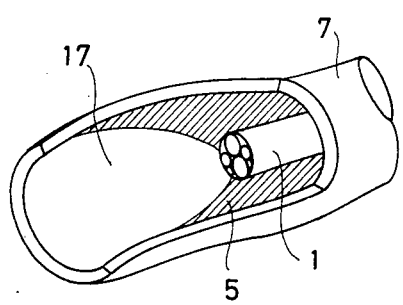
FIG. 2 is a diagram illustrating the way in which observations are made with the conventional fiberscope.
Figure 3:
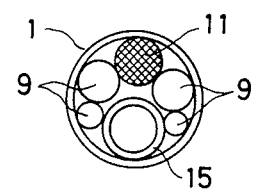
FIG. 3 is a cross-sectional view of one example of a conventional fiberscope.
Figure 4:
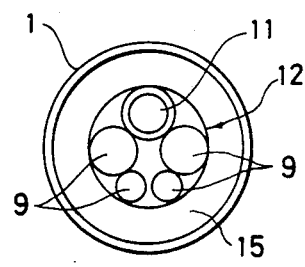
FIG. 4 is a cross-sectional view of another example of a conventional fiberscope.
Figure 5:
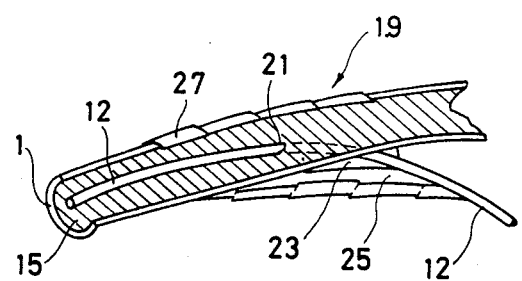
FIG. 5 is a perspective view, partially as a sectional diagram, showing the structure of a branching section of the fiberscope of FIG. 1.
Figure 11:
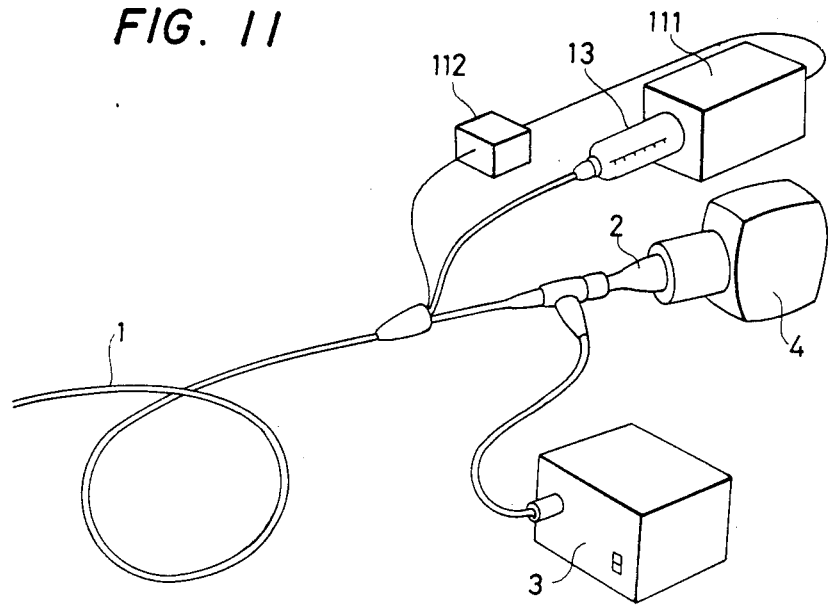
FIG. 11 is an external view of a fiberscope constructed according to the present invention.

A fiberscope of the invention will now be described with reference first to FIG. 11. In the fiberscope of FIG. 11, a flexible cable is provided with a device for sensing the flow rate of the surrounding fluid, and a flow rate processing unit 112 produces an output signal representative thereof. The output signal of the unit 112 is applied to operate an injecting unit 111 to cause a syringe 13 to inject physiological saline. The syringe 13 injects the physiological saline through a flush guide 106 provided between the flexible cable 1 and an image pickup section 107 provided at the top of the light guide and image fiber.

Figure 12:
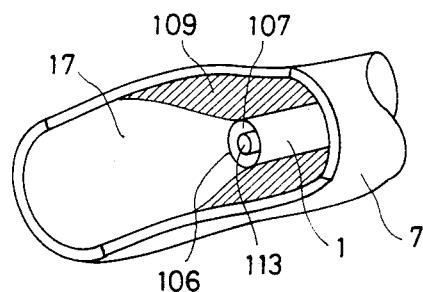
FIG. 12 is a diagram illustrating the way in which observations are carried out with the fiberscope of the invention.
Figure 13:
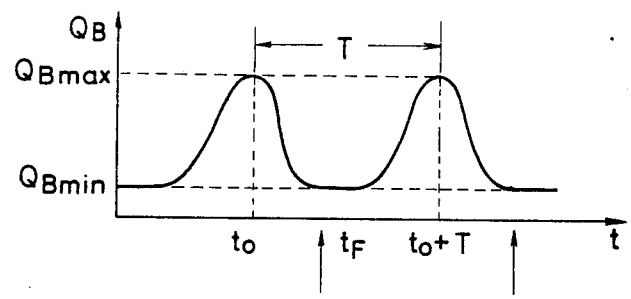
FIG. 13 is a diagram showing variations of blood flow rate with time and the flushing method employed.

FIG. 12 shows the end portion of a fiberscope in a blood vessel 7 and the surrounding area. The head 113 of a flow sensor is attached to the end of the fiberscope. The flow rate of blood varies at the patient's pulse rate as indicated in FIG. 13. (Such an effect is described by Sugawara, "Fluid Dynamics of Blood Vessels", *Japanese Mechanical Society Journal*, Vol. 85, No. 763 (June 1982).) To produce a clear region, injection of the saline solution should be started at a flow rate somewhat larger than $Q_{Bmin}$ at the time instant $t_F$ during the period T.

FIG. 14 is a block diagram showing a flush control device using a pressure sensor instead of a flow sensor. An output signal of the pressure sensor 114 is applied through a pressure rise/fall detector circuit 115 and a trigger circuit 116 to an injecting unit control section 118 to start or stop the latter. Furthermore, the pressure sensor 114 applies flow rate data through a flow rate calculating circuit 117 to the control section 118.

As shown in FIG. 15, the blood pressure P varies with the blood flow rate $Q_B$. (As the flow rate increases, the pressure decreases.) Accordingly, the total volume $V \simeq Q_F \Delta$ of the flush of saline solution should be calculated with a flow rate $Q_F^*$ slightly larger than $Q_{Bmin}$ for a period $\Delta$ from the instant $t_F$ of rise of the pressure P. In FIG. 15, $t_F + \Delta$ designates the instant of fall of the pressure P.

FIGS. 16 and 17 show the structure of the end portion of a specific example of a fiberscope according to the invention. Light guiding optical fibers 119 are arranged around an image transmitting system formed of an image fiber 124 and a lens 120. Formed near the fibers is a pressure sensor including a light transmitting optical fiber 122, a light receiving optical fiber 123 and a diaphragm 121 which is deformable with pressure. Variation of the distance between the inside surface of the diaphragm, that is, between its reflecting surface and the end face of the above-described optical fiber, varies the amount of light received by the light receiving optical fiber 123. Light applied to the light transmitting optical fiber may be obtained from the illuminating light source of the fiberscope. Optionally, a flow meter utilizing, for instance, the Doppler effect may be employed. Reference numeral 125 denotes a sleeve.

The fiberscope according to the invention has the following effects:

(1) As the flow rate required is small, the pressure at which the saline solution is injected can be made small.

(2) For the same reason, the outside diameter of the flexible cable can be made small, and therefore the applications of the fiberscope are increased.

(3) As the flush may be small both in flow rate and in volume, the adjacent tissue is little affected by the flush.

(4) The pressure sensor or flow sensor in the fiberscope provides additional data, which contributes to an improvement of the efficiency of diagnosis.

Particularly, the fiberscope of the invention may be used as:

(1) a fiberscope for inspecting the inside of a blood vessel or the heart, or (2) a fiberscope for inspecting the inside of a pipe in which opaque liquid such as crude oil or other chemicals flows.

Figure 18:
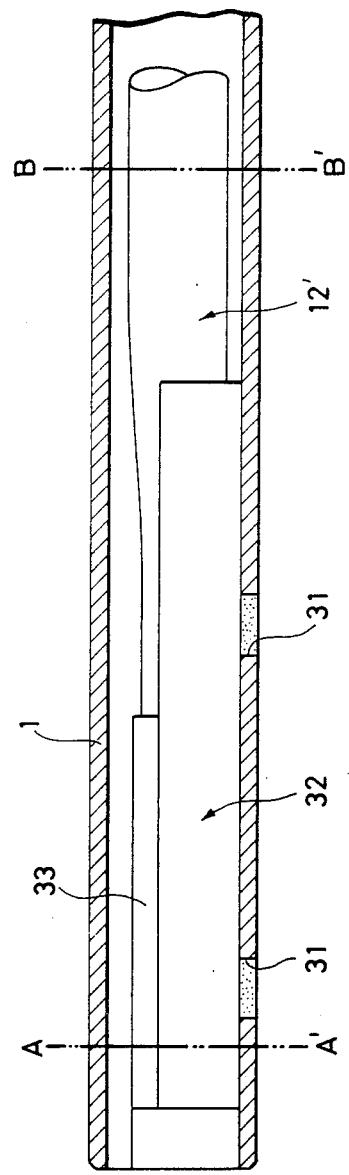
FIGS. 18 through 20 are diagrams showing the structure of a fiberscope according to this invention.
Figure 20:
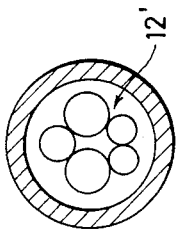
Figure 19:
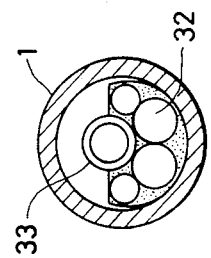
Figure 21:
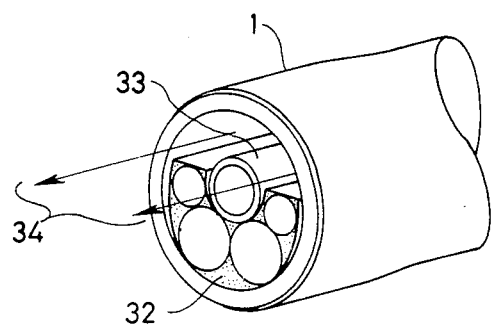
FIG. 21 is a perspective view of the front end portion of another embodiment of a fiberscope constructed according to the invention.

Another example of a fiberscope according to the invention will be described with reference to FIGS. 18 through 24. FIGS. 18, 19 and 20 are diagrams showing the structure of the front end portion thereof, and FIG. 21 is a perspective view of the front end portion. An image pickup adapter 33 coupling an image forming lens to the front end of an image fiber is fixedly bonded to the recess of a front end molded member 32 (manufactured according to a method described below) to hold illuminating light transmitting light guides. The outer wall of the front end molded part is fixedly bonded to the inner wall of a cover tube 1 2.8 mm in outside diameter and 2.2 mm in inside diameter and made of polyethylene resin or vinyl chloride resin. FIGS. 19 and 20 are sectional views taken along lines A—A' and B—B', respectively, in FIG. 18. The adhesion of the outer wall of the front end molded part 32 to the cover tube 1 is reinforced by filling cover tube bonding holes 31 with an epoxy adhesive to overcome the shock which occurs when a flush of physiological saline is injected. In FIG. 21, a flush flow 34 is formed in this manner. In addition, in order to efficiently remove the blood from the region in front of the image forming lens and the illuminating light transmitting light guides, the front end molded part is slightly retracted from the front end face of the cover tube.

Figure 22:
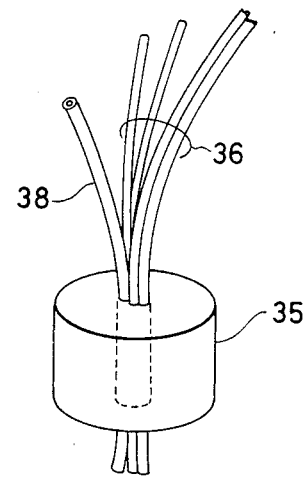
FIGS. 22 through 24 are explanatory diagrams used for a description of a method of manufacturing the front end portion of the fiberscope according to the invention.
Figure 23:
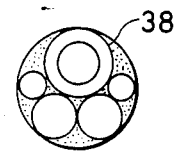
Figure 24:
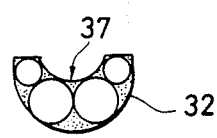

FIGS. 22, 23 and 24 illustrate the aforementioned method of manufacturing the front end molded part. As shown in FIG. 22, a metal mold made of a resin such as Teflon ™ having a through-hole 2 mm in diameter and 10 mm in length is prepared. Then, a bundle of plastic fibers used as the illuminating light transmitting light guides and a dummy tube 38 made of a resin such as Teflon TM for forming the recess 37 (FIG. 24) in the front end molded part 32 are inserted into the through-hole of the mold. The gap in the through-hole of the mold is filled with a resin such as an epoxy resin to form a preliminary part. After the resin has solidified, one end face of the preliminary part is polished, and the preliminary part is then removed from the metal mold 35. As a result, the preliminary part thus formed has one end face as shown in FIG. 23. Thereafter, the dummy tube 38 is removed, and then the preliminary part is partially cut so that the end face is as shown in FIG. 24.

As is apparent from the above description, according to the invention, the following effects are obtained:

(1) It is unnecessary to use intricate parts to secure the end portion. Therefore, the manufacturing cost of the fiberscope is significantly reduced.

(2) The end portion can be readily processed, and the outside diameter of the insertion part of the fiberscope can be reduced.

(3) Filling the holes cut in the cover tube with adhesive allows the front end molded part of the optical fiber bundle to be strongly bonded to the inner wall of the cover tube so that the optical fiber bundle will not be dislodged by the shock which occurs when a flush of physiological saline is injected.

Figure 25:
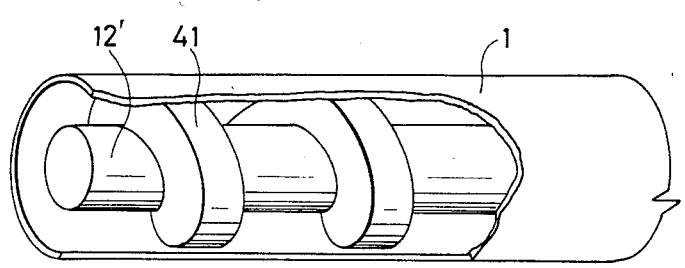
FIGS. 25 and 26 are perspective views, with parts cut away, showing further examples of a fiberscope of the invention.

Still another embodiment of the invention will be described with reference to FIGS. 25 through 28. FIG. 25 is a perspective view, with parts cut away, showing a fiberscope according to the invention.

Figure 26:
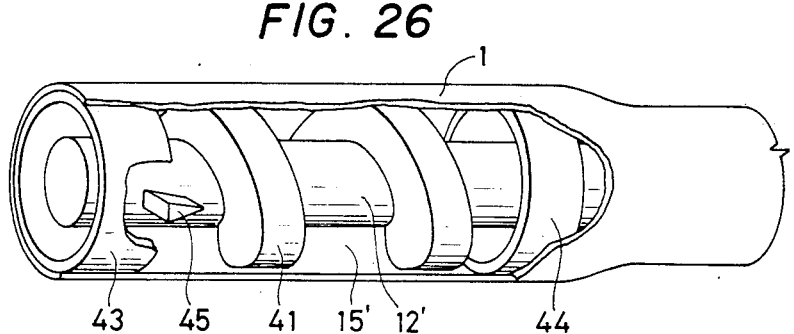
Figure 27:
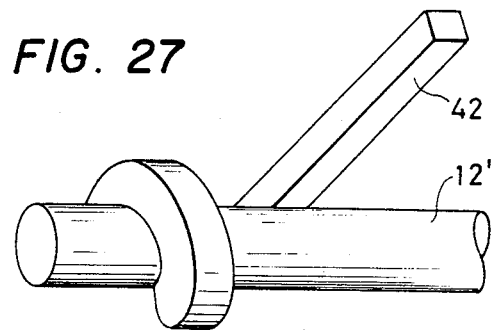
FIG. 27 is a diagram showing a method of the invention of forming a spiral spacer by winding a belt-shaped flexible member on the front end portion of a fiber bundle.

A spiral spacer 41 is laid around the end portion of a fiber bundle 12 including image transmitting image fibers having at the end thereof an optical system for forming the image of an object. The spacer 41 is arranged between the outer wall of the fiber bundle 12' and the inner wall of a cover tube 1. The spiral spacer is a flexible belt-shaped member 42 made of vinyl chloride or the like which is bonded to the fiber bundle while being spirally wound thereon as shown in FIG. 26. Since the contact areas of the bonding surfaces of the spiral spacer can be made large, the spiral spacer can be readily and positively bonded to the fiber bundle. After being bonded to the fiber bundle 12', the spiral spacer 41 is bonded to the inner wall of the cover tube 1. Thus, the cover tube 1 and the fiber bundle 12' are secured to each other through the spacer.

Figure 28:
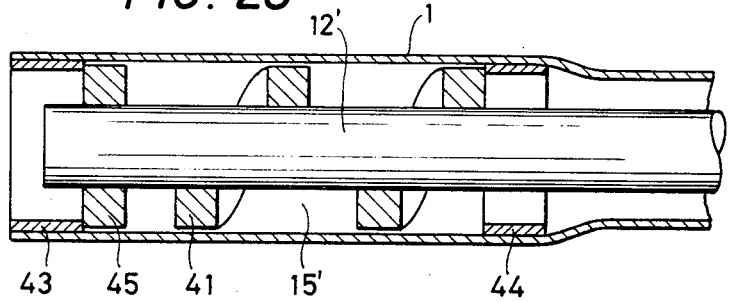
FIG. 28 is a longitudinal sectional view of the fiberscope of FIG. 26 viewed from above.

In the case where the spiral spacer is not sufficiently bonded to the cover tube, a fixing technique such as that illustrated in FIGS. 26 and 28 may be employed. In this case, two rings, namely a front ring 43 and a rear ring 44, are provided so that the spiral spacer 41 fixed to the fiber bundle 12' cannot be moved back and forth in the axial direction due to the pulsating flow of transparent liquid in the liquid guide passageway 15' in the cover tube 1. The rings 43 and 44 are made of a material which can be bonded positively to the cover tube 1, and therefore they can be fixedly bonded to the cover tube. However, as the rings 43 and 44 are merely in contact with the peripheral parts of the front and rear end faces, respectively, of the spiral spacer 41, when the liquid is injected, the end portion of the fiber bundle 12' is shocked, causing movement in the cover tube, which may result in the end of the spiral spacer 41 being disengaged from the end face of the front ring 43 and springing out forwardly.

In order to prevent this from happening, a stop 45 is provided at a position on the outer wall of the fiber bundle 12' 180° opposite the position of the end face of the spiral spacer engaged with the front ring 43. It is preferable that the stop 45 be in the form of a prism disposed with one edge against the flow of liquid. As is apparent from FIGS. 26 and 28, the end portion of the cover tube 1 is made larger in sectional area than the other portion so as to make the liquid guide passageway 15' as large as possible. In this case, it may be unnecessary to fixedly bond the rear ring 44 to the cover tube 1. The spiral spacer 41 fixed to the end portion of the fiber bundle 12' can be secured directly through the front and rear rings 43 and 44 to the cover tube 1 as described above. With any one of the above-described techniques, the bonding area is larger than that in conventional arrangement in which a small but intricately configured cap is bonded to the cover tube. Therefore, in accordance with the invention, the bonding operation can be achieved readily and positively. Thus, the drawback of the conventional fiberscope of the possibility of the cap being dislodged by the shock caused when the liquid is injected is eliminated.

As is clear from the above description, in the fiberscope according to the invention, a spiral spacer made of belt-shaped flexible material is secured to the outer wall of the front end portion of the fiber bundle, including the image transmitting image fiber along with its associated optical system and illuminating light transmitting light guides arranged along the image fibers. The spiral spacer extends in the axial direction of the fiber bundle in the liquid passageway formed between the outer wall of the fiber bundle and the inner wall of the cover tube which covers the fiber bundle. The manufacturing cost of the fiberscope according to the invention is much lower than that of the conventional fiberscope requiring a cap having a high manufacturing cost and intricate construction.

As the liquid passageway is spiral, the liquid is injected with a spiral flow, which contributes to the quick displacement of the opaque liquid in the region under observation.

Figure 29:
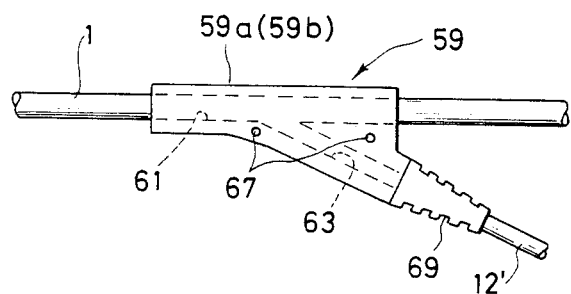
FIG. 29 is a side view showing a part of a fiberscope with a branching mount.
Figure 30:
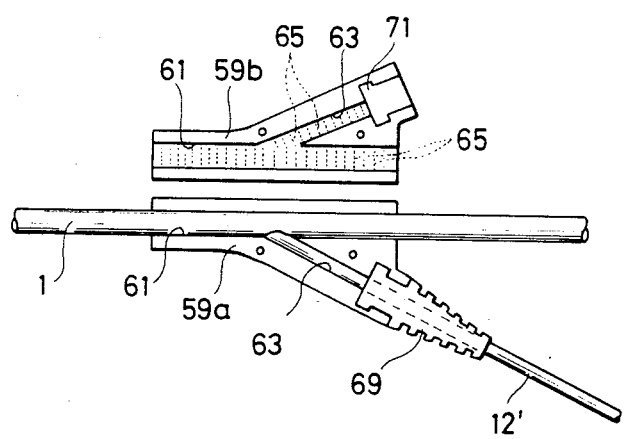
FIG. 30 is a diagram, similar to FIG. 29, showing components of the branching mount.

Next, a branch portion of the fiberscope of the invention will be described. In the embodiment shown in FIGS. 29 and 30, a substantially Y-shaped rigid branching mount 59 is used to cover and seal the branching section of the flexible tube 1 and the fiber bundle 12'. The branching mount 59, as shown in these figures, is made up of two parts, namely, upper and lower halves 59b and 59a of a substantially symmetrical configuration. The branching mount 59 has a tube guide passageway 61 which maintains the flexible tube 1 straight and a fiber guide passageway 63 for accommodating the fiber bundle 12'.

The fiber guide passageway 63 branches from the tube guide passageway 61. The halves 59a and 59b of the branching mount 59 can be formed by aluminum casting or resin molding. Each of the guide passages 61 and 63 has a number of grooves 65 which extend substantially perpendicularly to the axial direction. Therefore, when the halves 59a and 59b are joined together, they engage the outer walls of the flexible tube 1 and the fiber bundle 12' to positively hold them. A water-resistant adhesive is applied to the guide passageways 61 and 63 and the outer walls of the flexible tube 1 and the fiber bundle 12' which are laid along the guide passageways. When the adhesive is solidified, it mechanically locks the tube 1 and the fiber bundle 12' to the branching mount 59 and forms a positive seal at the branching section. The halves 59a and 59b of the branching mount, after being positioned properly, are joined together with screws 67. In order to reinforce the fiber bundle 12' pulled out through the passageway 63, a rubber bushing 69 having a passage for receiving the fiber body is provided at the outlet of the fiber guide passageway 63 of the mount 59. For this purpose, a holding structure 71 (which takes the form of an annular groove in the figures) for holding an end portion of the bushing 69 is formed at the outlet of the passageway 63. Such a rubber bushing may be provided at the outlet of the passageway for the flexible tube 1 in the branching mount 59.

The branching section thus constructed is rigid because it is covered in its entirety by the rigid branching mount. The seal is positive because the tube 1 and the fiber bundle 12' cannot move appreciably in the branching mount 59 when the branching section is covered by the branching mount. The branching mount 59 can be manufactured at a low cost by a casting or resin molding process. The formation of the branching section is considerably simple because it can be achieved merely by joining the halves of the branching mount to which adhesive has been applied. In addition, the optical fiber can be sufficiently reinforced by providing the rubber bushing 59 at the outlet of the branching mount.

Embodiments of the invention have been described with reference to a medical fiberscope for observing or measuring the inside of a blood vessel or the heart. However, it should be noted that the invention is not limited thereto or thereby. That is, for instance, the fiberscope according to the invention may be used to observe or measure the inside of a pipe or tank containing an opaque liquid such as crude oil.

As is apparent from the above description, the fiberscope according to the invention has a branching section composed of a flexible tube and a fiber body which has a rigid structure, provides a positive seal, and can be readily manufactured at a low cost.

We claim:

1. In a fiberscope for conducting observations in a region ordinarily filled with an opaque liquid and including a fiber bundle comprising an image transmitting image fiber having an optical system at a forward end thereof for forming an image of an object under observation and illuminating light transmitting light guides arranged beside said image fiber; a cover tube covering said fiber bundle; and a liquid passageway formed between an inner wall of said cover tube and outer surfaces of said fiber bundle, the improvement comprising: means for injecting transparent liquid from a hole near the end of said fiberscope at a flow rate in synchronization with variations in a flow rate of said opaque liquid to temporarily displace some of said opaque liquid, thereby to permit observation.

2. The fiberscope as claimed in claim 1, wherein said injecting means comprises means for measuring a pressure of said opaque liquid.

3. The fiberscope as claimed in claim 2, wherein said injecting means further comprises means for injecting said transparent liquid in an amount determined in accordance with said pressure.

4. The fiberscope as claimed in claim 2, wherein said transparent liquid comprises physiological saline, and wherein injection is in synchronization with a heartbeat.

5. The fiberscope as claimed in claim 1, wherein said injecting means comprises means for measuring a flow velocity of said opaque liquid.

6. The fiberscope as claimed in claim 5, wherein said injecting means further comprises means for injecting said transparent liquid in an amount determined in accordance with said flow velocity.

7. The fiberscope as claimed in claim 5, wherein said transparent liquid comprises physiological saline, and wherein injection is in synchronization with a heartbeat.

8. The fiberscope as claimed in claim 1, wherein said flow rate of said opaque liquid has periodic high and low values, injection of said transparent liquid occurring in synchronization with periodicity of said low values.

* * * * *